United States Patent [19]

Gilligan

[11] Patent Number: 5,631,406
[45] Date of Patent: May 20, 1997

[54] CHEMICAL COMPOUNDS

[75] Inventor: William H. Gilligan, Ft. Washington, Md.

[73] Assignee: The United States of America as represented by the Secretary of the Navy, Washington, D.C.

[21] Appl. No.: 256,462

[22] Filed: Mar. 30, 1981

[51] Int. Cl.$^6$ ............ C07C 43/303; C07C 43/313
[52] U.S. Cl. ............ 568/604; 568/594; 568/944; 568/945; 568/946; 149/88
[58] Field of Search ............ 149/88; 260/463; 568/590, 594

[56] References Cited

U.S. PATENT DOCUMENTS

| | | | |
|---|---|---|---|
| 3,306,939 | 2/1964 | Hill | 260/644 |
| 3,922,311 | 11/1975 | Peters et al. | 568/590 |
| 4,120,710 | 10/1978 | Peters et al. | 149/88 |

*Primary Examiner*—Charles T. Jordan
*Assistant Examiner*—John R. Hardee
*Attorney, Agent, or Firm*—John Forrest; Roger D. Johnson

[57] ABSTRACT

Dichloroformals of the formula $$(RCH_2O)_2CCl_2$$

wherein R is $-C(NO_2)_3$, $-CF(NO_2)_2$, $-CF_2(NO_2)$, $-CCl(NO_2)_2$, $-C(NO_2)_2CH_3$, $-CCl_3$, $-CF_3$, or $-CF_2CF_3$. These dichloroformals are prepared by reacting the corresponding thionocarbonate of the formula $$(RCH_2O)_2C=S,$$

wherein R is as defined above, with sulfuryl chloride in the presence of a Friedel-Craft catalyst (e.g., $AlCl_3$ or $TiCl_4$). Another method is to react the thionocarbonate with chlorine gas in the presence of a polar additive such as 2,2,2-trifluoroethanol or acetonitrile. These energetic dichloroformals are useful as explosive and propellant ingredients and as intermediates in the synthesis of other energetic explosive and propellant ingredients.

15 Claims, No Drawings

CHEMICAL COMPOUNDS

BACKGROUND OF THE INVENTION

This invention relates to energetic organic compounds and more particularly to halo- and nitroalkyldichloroformals.

U.S. Pat. No. 3,306,939, entitled "Orthoesters 2,2,2-Trinitroethanol," which issued to Marion E. Hill on Feb. 28, 1967, suggests bis(2,2,2-trinitroethyl)dichloroformals as a transitory intermediate in the synthesis of trinitroethyl orthocarbonate from 2,2,2-trinitroethanol and carbon tetrachloride in the presence of ferric chloride. The dichloroformal was neither isolated nor actually identified. Given the reactivity of the dichloroformal under those conditions, the method is unsuitable for the synthesis of bis(polynitroalkyl) dichloroformals. We have found no other reference to bis (polynitroalkyl)dichloroformals in the literature. While various methods are known to convert ketones, aldehydes and certain esters to dichloro compounds, these methods are ineffective in converting carbonates to the halo-, nitro-, and halonitroalkyl substituted dichloroformals. Because these compounds would be useful as energetic explosive and propellant ingredients and as intermediates in the synthesis of other energetic explosive and propellant compounds, it would be desirable to synthesize them.

SUMMARY OF THE INVENTION

Accordingly, an object of this invention is to provide novel organic compounds.

Another object of this invention is to provide novel energetic explosive and propellant ingredients.

A further object of this invention is to provide novel intermediates for the synthesis of new explosive compounds.

Yet another object of this invention is to provide a method of synthesizing new energetic compounds.

These and other objects of this invention are achieved by providing compounds of the formula $$(RCH_2O)_2CCl_2$$

wherein R is selected from the group consisting of —C(NO$_2$)$_3$, —CF(NO$_2$)$_2$, —CF$_2$(NO$_2$), —CCl(NO$_2$)$_2$, —C(NO$_2$)$_2$CH$_3$, —CCl$_3$, —CF$_3$, and —CF$_2$CF$_3$, which are prepared by refluxing the corresponding thionocarbonate of the formula $$(RCH_2O)_2C=S$$

with sulfuryl chloride in the presence of a Friedl-Crafts catalyst such as AlCl$_3$ or TiCl$_4$. Another method of preparing the dichloroformal is to dissolve the thionocarbonate in a mixture of a chlorinated hydrocarbon solvent and a polar additive (such as trifluoroethanol or acetonitrile) and bubble chlorine gas through the solution at ambient temperature. These substituted dichloroformals are useful as energetic explosive and propellant ingredients, and as intermediates for the preparation of energetic organic explosive compounds, additives, and plasticizers.

DETAILED DESCRIPTION OF THE INVENTION

Thionocarbonates of the formula

[C(NO$_2$)$_3$CH$_2$O]$_2$C=S,

[CF(NO$_2$)$_2$CH$_2$O]$_2$C=S,

[CF$_2$(NO$_2$)CH$_2$O]$_2$C=S,

[CCl(NO$_2$)$_2$CH$_2$O]$_2$C=S,

[CH$_3$C(NO$_2$)$_2$CH$_2$O]$_2$C=S,

[CCl$_3$CH$_2$O]$_2$C=S,

[CF$_3$CH$_2$O]$_2$C=S, and

[CF$_3$CF$_2$CH$_2$O]$_2$C=S, are used to synthesis dichloroformals of the formulas

[C(NO$_2$)$_3$CH$_2$O]$_2$CCl$_2$,

[CF(NO$_2$)$_2$CH$_2$O]$_2$CCl$_2$,

[CF$_2$(NO$_2$)CH$_2$O]$_2$CCl$_2$,

[CCl(NO$_2$)$_2$CH$_2$O]$_2$CCl$_2$,

[CH$_3$C(NO$_2$)$_2$CH$_2$O]$_2$CCl$_2$,

[CCl$_3$CH$_2$O]$_2$CCl$_2$,

[CF$_3$CH$_2$O]$_2$CCl$_2$, and

[CF$_3$CF$_2$CH$_2$O]$_2$CCl$_2$.

The usual chlorinating agents such as chlorine in hydrocarbons or chlorinated solvents (usual conditions), sulfuryl chloride, thionyl chloride, phosphorous (V) chloride etc., were also ineffective in converting thionocarbonates to dichloroformals. It appeared that a weak chlorine complex would be formed which would revert to starting material upon attempted isolation.

The conversion was finally effected by chlorination with sulfuryl chloride and using a Friedel-Crafts catalyst such as AlCl$_3$ or titanium tetrachloride.

$$[FC(NO_2)_2CH_2O]_2C=S \xrightarrow[\text{reflux}]{\text{AlCl}_3 \text{ or TiCl}_4 / SO_2Cl_2} [FC(NO_2)_2CH_2O]_2CCl_2$$

The best yield obtained by this method was 71% using titanium (IV) chloride as catalyst and refluxing for five days. With aluminum chloride as catalyst the reflux time was much less but the yields were lower ranging in a number of experiments from 30 to 50% of bis(2-fluoro-2,2-dinitroethyl)dichloroformal.

A preferred method of preparing the halo- , nitro- , and halonitroalkyldichloroformals is to bubble chlorine gas through a stirred mixture of the appropriate thionocarbonate, a chlorinated hydrocarbon and a polar additive (such as trifluoroethanol or acetonitrile) at ambient temperature. In general the reaction is carried out by making up a 20% (w/v) slurry or solution of the thionocarbonate in a chlorinated hydrocarbon such as carbon tetrachloride, methylene chloride, chloroform, or 1,2-dichloroethane. About 2 moles of polar additive per mole of thionocarbonate is added and chlorine gas is passed through the stirred solution or slurry for from 3 to 8 hours at ambient temperature, after initial cooling. The polar additive can be used as a pure chlorinating medium (e.g., trifluoroethanol) but surprisingly the reaction is slower under these conditions. Furthermore, since the polar additive is higher in cost than the hydrocarbons, it is preferable to use as little as possible. The additive should be unreactive to chlorine and the other reactants and products.

The role of the additive in the reaction is not clear, but it may aid in the ionization of the chlorine; increasing the polarity of a medium generally has little effect on free radical reactions. Nitroalcohols can also be used as additives but the cost of these compounds preclude their use.

The temperature at which the reaction is performed can vary over wide limits, from ice bath to reflux. However, at ice bath temperature the reaction is slow, while at higher temperatures there is a greater chance of side-reactions involving the additive. The preferred temperature range is 15°–25° C.

The following methods of preparing the thionocarbonate starting materials are incorporated from U.S. Pat. No. 4,323,518, entitled "Polynitroethylthionocarbonates and Method of Preparation," which issued on Apr. 6, 1982, to William H. Gilligan.

With the exception of bis(3,3,3-trinitroethyl) thionocarbonate, the thionocarbonates are synthesized by reacting one mole of 1,1-thiocarbonyl-di-1,2,4-triazole with two moles of the appropriate alcohol in a chlorinated hydrocarbon solvent or acetone under mild basic conditions at ice bath (0° C.) to room temperature (25° C.) with or without a catalytic amount of pyridine. Examples 1 and 3 illustrate this method. Alcohols which are used include 2-fluoro-2,2-dinitroethanol,
2,2-difluoro-2-nitroethanol,
2-chloro-2,2-dinitroethanol,
2,2-dinitropropanol,
2,2,2-trichloroethanol,
2,2,2-trifluoroethanol, and
2,2,3,3,3-pentafluoropropanol.

Example 2 illustrates a method by which bis(3,3,3-trinitroethyl)thionocarbonate is prepared from 1,1'-thiocarbonyl-di-1,2,4-triazole and 2,2,2-trinitroethanol. In this method trifluoroacetic acid is added to tie up the 1,2,4-triazole as it is liberated. This prevents or minimizes the destructive side reactions which would otherwise occur between the 1,2,4-triazole and 2,2,2-trinitroethanol.

To more clearly illustrate this invention, the following examples are represented. It should be understood, however, that these examples are presented merely as a means of illustration and are not intended to limit the scope of the invention in any way.

EXAMPLES

Examples 1 through 3 are included to illustrate the method by which the thionocarbonate starting materials are prepared from conventional ingredients.

EXAMPLE 1

Bis(2,2-dinitropropyl)thionocarbonate

To a solution of 4.50 g (0.03 mol) of 2,2-dinitropropanol in 50 ml of acetone was added 4.90 g (0.027 mol) of 1,1'-thiocarbonyl-di-1,2,4-triazole and 0.5 ml of pyridine. After standing at ambient temperature for two days, the acetone was removed on a rotavac and the solid residue was thoroughly washed with water. After air drying, the crude product was recrystallized from chloroform to give 4.27 g (83%) of product, mp 86°–7°.

EXAMPLE 2

Bis(3,3,3-trinitroethyl)thionocarbonate

A methylene chloride solution (100 ml), containing 5.07 g (28 mmol) of trinitroethanol, 3.20 g (28 mmol) of trifluoroacetic acid and 2.50 g (14 mmol) of 1,1'-thiocarbonyl-di-1,2,4-triazole, was stirred at ambient temperature for 14 days. The solution was then washed with three 100 ml portions of water, dried with magnesium sulfate, filtered and the volatiles removed on a rotavoc. The residual oil was washed several times with water by decantation until the oil solidified. The crude product, after drying, was chromotographed on silica gel and eluted with methylene chloride/hexane (1/1) to give it the initial eluates 1.1 g (20%) of a white crystalline product, m.p. 92°–3°.

EXAMPLE 3

Bis(2,2-fluoro-2-nitroethyl)thionocarbonate

To a solution of 5.59 g (44.0 mmol) of 2,2-difluoro-2-nitroethanol and 3.60 g (20.0 mmol) of 1,1'-thiocarbonyl-di-1,2,4-triazole in 50 ml of dry methylene chloride was added 0.5 ml pyridine. The solution, after stirring for two hours, was washed with five 100 ml portions of water. After drying with magnesium sulfate and filtering, the volatiles were removed in vacuo the residue was distilled through a short path apparatus to give 4.2 g (71%) of product, b.p. about 63°/0.1 torr.

Although dry methylene chloride was used as the solvent for the reactions in these examples, other inert chlorohydrocarbon solvents, such as chloroform, 1,2-dichloroethane, and 1,1,2-trichloroethane, may also be used.

The reactions are carried out in a temperature range of from 0° C. to 25° C. (ambient room temperature). It is preferable to mix the reactants together at the lower end of this temperature range to prevent overheating and then complete the reaction at ambient room temperature.

Examples 4 through 9 are presented to illustrate the preparation of the compounds of the present invention.

EXAMPLE 4

Bis(2-fluoro-2,2-dinitroethyl)dichloroformal

To a solution of 10.0 g (28.6 mmol) of bis(2-fluoro-2,2-dinitroethyl) thionocarbonate in 50 ml of freshly distilled sulfuryl chloride was added 4.0 ml of titanium tetrachloride. The solution was then refluxed for 5 days. Excess sulfuryl chloride and titanium tetrachloride were then removed in vacuo at a bath temperature of 50°. The solid residue was recrystallized from chloroform to give 7.91 g (71%) of bis(fluorodinitroethyl)dichloroformal as colorless crystals, mp-57–58.

H-NMR(CDCl$_3$/TMS)$\delta$(ppm)-d, 5.02.

Calc. for $C_5H_4Cl_2F_2N_4O_{10}$. C, 15.44; H, 1.04; Cl, 18.23; F, 9.77; N, 14.40. Found: C, 15.46; H, 1.05; Cl, 18.40; F, 9.98; N, 14.11.

EXAMPLE 5

Chlorination of Bis(2-fluoro-2,2-dinitroethyl) thionocarbonate With Gaseous Chlorine in Carbon tetrachloride/trifluoroethanol Gaseous chlorine was slowly passed into a stirred slurry of 21.0 g (0.067 mol) of bis 2-fluoro-2,2-dinitroethyl) thionocarbonate in 100 ml of dry carbon tetrachloride and 10 ml of dry trifluoroethanol for 4.5 hours at the end of this period the slurry had changed into a clear orange-colored solution. After standing overnight, volatiles were removed on a rotovac and the solid residue was recrystallized from chloroform to give 19.33 g (83%) of bis(2-fluoro-2,2-dinitroethyl)dichloroformal, m. p. 57°–8°.

EXAMPLE 6

Bis(2,2-dinitropropyl)dichloroformal

Gaseous chlorine was passed into a solution of 3.1 g (9.1 mmol) of bis(2,2-dinitropropyl)thionocarbonate in 7 ml of acetonitrile/1,2-dichloroethane (3/4; v/v) for 5 ½ hours. After standing overnight, the solvents were removed and the solid residue recrystallized from 1,2-dichloroethane to give 3.2 g (93%) of product, m. p. 121°–3°.

H-NMR(acetone-$Cl_6$/TMS)$\delta$(ppm)-s, 5.04; s, 2.39.

Calc for $C_7H_{10}N_4O_{10}Cl_2$. C, 22.06; H, 2.65; Cl, 18.61. Found. C, 22.30; H, 2.68; Cl, 18.28.

EXAMPLE 7

Bis(2,2,2-trinitroethyl)dichloroformal

Gaseous chlorine was slowly passed into a stirred solution of bis(2,2,2-trinitroethyl)thionocarbonate(4.20 g) in 11 ml of acetonitrile/1,2-dichloroethane, (3/8; v/v) for 6 hours. After standing overnight, the volatiles were removed in vacuo. The solid residue was recrystallized from 1,2-dichloroethane/hexane to give 4.33 g white crystals (96%); mp 75°–77°.

H-NMR($CDCl_3$)$\delta$(ppm). s, 5.19.

Calc. for $C_5H_4Cl_2N_6O_{14}$. C, 13.55; H, 0.91; Cl, 16.01; N, 18.97. Found. C, 13.69; H, 0.99; Cl, 15.89; N, 18.74.

EXAMPLE 8

Bis(2,2-difluoro-2-nitroethyl)dichloroformal

Gaseous chlorine was passed into a stirred solution of 11.95 g (0.04 mol) of bis(2,2-difluoro-2-nitroethyl) thionocarbonate in 21 ml of acetonitrile/1,2-dichloroethane (6/15; v/v) for 6.5 hours. After filtering off a small amount of white precipitate, volatiles were removed on a rotavac. The residual oil was distilled to give 10.89 g (81%) of product; b. p. 85°/1.0 torr.

H-NMR($CDCl_3$/TMS)$\delta$(ppm)-t, 4.73.

Calc. for $C_5H_4Cl_2F_4N_2O_6$. C, 17.93; H, 1.20; Cl, 21.17; F, 22.69; N, 8.36. Found. C, 17.82; H, 1.27; Cl, 21.32; F, 22.37; N, 8.37.

EXAMPLE 9

Bis(2,2,2-trifluoroethyl)dichloroformal

Gaseous chlorine was passed into a stirred solution of 42.7 g (0.176 mol) of bis(2,2,2-trifluoroethyl) thionocarbonate in 75 ml acetonitile/1,2-dichloroethane (1/2; v/v) for 6 hours. After distilling off the solvent, the product was collected at 68°–72°/80 torr; 43.3 g. (93%).

H-NMR($CDCl_3$/TMS)$\delta$(ppm)-q.

Calc. for $C_5H_4Cl_2F_6O$. C, 21.37; H, 1.44; Cl, 25.24; F, 40.57. Found. C, 21.44; H, 1.43; Cl, 25.18; F, 40.35.

Obviously, many modifications and variations of the present invention are possible in light of the above teachings. It is therefore to be understood that within the scope of the appended claims the invention may be practiced otherwise than as specifically described.

What is claimed is:

1. A substituted dichloroformal of the formula $$(RCH_2O)_2CCl_2$$

wherein R is selected from the group consisting of —$C(NO_2)_3$, —$CF(NO_2)_2$, —$CF_2(NO_2)$, —$CCl(NO_2)_2$, —$C(NO_2)_2CH_3$, —$CCl_3$, —$CF_3$, and —$CF_2CF_3$.

2. The dichloroformal of claim 1 which is bis(2,2,2-trinitroethyl)dichloroformal.

3. The dichloroformal of claim 1 which is bis(2-fluoro-2,2-dinitroethyl)dichloroformal.

4. The dichloroformal of claim 1 which is bis(2,2-difluoro-2-nitroethyl)dichloroformal.

5. The dichloroformal of claim 1 which is bis(2,2,2-trifluoroethyl)dichloroformal.

6. The dichloroformal of claim 1 which is bis(2,2-dinitropropyl)dichloroformal.

7. A method of synthesizing dichloroformals of the formula $$(RCH_2O)_2CCl_2$$

by reacting a thionocarbonate of the formula $$(RCH_2O)_2C=S$$

with sulfuryl chloride in the presence of a Friedel-Crafts catalyst, wherein R is selected from the group consisting of —$C(NO_2)_3$, —$CF(NO_2)_2$, —$CF_2(NO_2)$, —$CCl(NO_2)_2$, —$C(NO_2)_2CH_3$, —$CCl_3$, —$CF_3$, and —$CF_2F_3$.

8. The method of claim 7 wherein the Friedel-Crafts catalyst is $AlCl_3$.

9. The method of claim 7 wherein the Friedel-Crafts catalyst is $TiCl_4$.

10. A method of synthesizing dichloroformals of the formula $$(RCH_2O)_2CCl_2$$

wherein R is selected from the group consisting by of —$C(NO_2)_3$, —$CF(NO_2)_2$, —$CF_2(NO_2)$, —$CCl(NO_2)_2$, —$C(NO_2)_2CH_3$, —$CCl_3$, —$CF_3$, and —$CF_2F_3$, comprising:

(1) Forming a mixture of
 (a) a chlorinated hydrocarbon,
 (b) a polar additive, and
 (c) a thionocarbonate of the formula $$(RCH_2O)_2C=S$$

wherein R is as defined above; and (2) passing chlorine gas through the mixture.

11. The method of claim 10 wherein the chlorinated hydrocarbon solvent is selected from the group consisting of carbon tetrachloride, methylene chloride, chloroform, 1,2-dichloroethane, and 1,1,2-trichloroethane.

12. The method of claim 10 wherein the polar additive is a 2-fluoro-2,2-dinitroethanol.

13. The method of claim 10 wherein the polar additive is acetonitrile.

14. The method of claim 10 wherein at least two moles of polar additive is used for each mole of the thionocarbonate.

15. The method of claim 10, 11, 12, 13, or 14 wherein the reaction temperature is from 15° C. to 25° C.

* * * * *